United States Patent
Fritz et al.

(10) Patent No.: US 6,515,119 B1
(45) Date of Patent: Feb. 4, 2003

(54) USE OF S-YDCB AND B-YDCB, ESSENTIAL BACTERIAL GENES

(75) Inventors: Christian Fritz, Natick; Philip Youngman; Luz-Maria Guzman, both of Boston, all of MA (US)

(73) Assignee: Millennium Pharmaceuticals, Inc., Cambridge, MA (US)

( * ) Notice: Subject to any disclaimer, the term of this patent is extended or adjusted under 35 U.S.C. 154(b) by 0 days.

(21) Appl. No.: 09/163,446

(22) Filed: Sep. 30, 1998

(51) Int. Cl.[7] .................. C07H 21/02; C07H 21/04; C12N 15/00; C12N 1/20; C12N 1/14
(52) U.S. Cl. .................. 536/23.7; 536/23.1; 435/252.3; 435/320.1; 435/254.2
(58) Field of Search .................. 536/23.1, 23.7, 536/24.5; 435/320.1, 243, 455, 252.3, 252.31, 173.1, 69.1, 7.34, 7.2, 254.2

(56) References Cited

U.S. PATENT DOCUMENTS 6,060,282 A * 5/2000 Tang et al. .................. 435/69.3

FOREIGN PATENT DOCUMENTS

| WO | WO9818931 A2 * | 5/1998 |
| WO | WO 98/26072 | 6/1998 |
| WO | WO 99/33871 | 7/1999 |

OTHER PUBLICATIONS

F Kunst et al.; "The Complete Genome Sequence of the Gram–Positive Bacterium *Bacillus subtilis*"; Mar. 30, 1998; Nature (London) XP–002128453.
Chemical Abstracts, vol. 128, No. 13, Mar. 30, 1998 Columbus, Ohio USA; abstract No. 150233, XP002128453.
Kunst et al. (1997), "The complete genome sequence of the gram–positive bacterium *Bacillus subtilis*" Nature (London), 390 (6657):249–256.
Ogasawara. Mar., 1997, EMBL database Accession No. AB001488.*
Emr. 1990. in Goeddel et al. Methods in Enzymology vol. 185, pp. 231–233.*
Gold. 1990. in Goeddel et al. Methods in Enzymology vol. 185, pp. 11–14.*
Beloin, C, et al, "Characterization of an Irp–like (IrpC) gene from *Bacillus subtilis*", Molecular General Genetics, vol. 256, pp. 63–71, Sep. 1997.*

* cited by examiner

Primary Examiner—Remy Yucel
Assistant Examiner—Konstantina Katcheves
(74) Attorney, Agent, or Firm—Fish & Richardson P.C.

(57) ABSTRACT

Disclosed are methods for using the essential genes and polypeptides "S-ydcB," found in *Streptococcus pneumoniae*, and "B-ydcB," found in *Bacillus subtilis*. These genes and polypeptides, as well as homologs and orthologs thereof, can be used to identify antibacterial agents for treating a broad spectrum of bacterial infections.

19 Claims, 4 Drawing Sheets

```
  1 TTGCCTAGTTGGGAAAATACAGAGGCCTTGGTAGAAGAGATTTATGTTACCTTGACAAAATAAGTGAAAAGGATGAGTTGGGAATCTCAACTCCTTT 100
    AACGGATCCAACCCTTTTATGTCTCCGGAACCATCTTCTAAATACAATGAACTGTTTTCATTTTATTCACTTTTCCTACCTTCAACCCCTTAGAGTTGAGGAAA

1 L  P  R  L  G  K  Y  R  G  L  G  R  R  D  L  C  Y  L  D  K  I  S  E  K  D  G  V  G  E  S  Q  L  L  L  34

101 TGATGAGAATGATAGTTGGACACGGAATTGACATCGAAGAATTGCTTCGATAGAAAGCGCAGTTACACGACATGAAGGATTTGCTAAGCGTGTACTGAC 200
    ACTACTCTTACTATCAACCTGTGCCTTAACTGTAGTTCTTAACGAAGCTATCTTTCGCGTCAATGTGCTGTACTTCCTAAACGATTCGCACATGACTG

35 M  R  M  I  V  G  H  G  I  D  I  E  E  L  A  S  I  E  S  A  V  T  R  H  E  G  F  A  K  R  V  L  T  67

201 CGCTCAGGAAATGAGAGCGCTTCACCAGTCTCAAAGGACGCAGGCAAATAGAATATTTAGCTGGTCGCTGGTCGGTCGGCTAAGGAGGCCTTTCCAAGGCTATG 300
    GCGAGTCCTTTACTCTCGCGAAGTGGTCAGAGTTTCCTGCCACCGTTCCGTTTATCTTATAAATCGACCAGCAGCCGATTCCTCCGGAAAAGGTTCCGATAC

68 A  Q  E  M  E  R  F  T  S  L  K  G  R  R  Q  I  E  Y  L  A  G  R  W  S  A  K  E  A  F  S  K  A  M  100

301 GGAACGGGGCATTAGCAAGCTTCGGTTTTCAGGATTTGGAAGTCTTGAACAATGAACTGTTACTGCACCCCGGAATAAAATCAGTCCGTGTAAAAGTCCTTTCTAAA 400
    CCTTGCCCCGTAATCGTTCGAAGCCAAAAGTCCTAAACTTCAGAACTTGTTACTTGACAATGACGTGGGGCCCTTATTTTAGTCAGGCACATTTTCAGGAAAGATTT

101 G  T  G  I  S  K  L  G  F  Q  D  L  E  V  L  N  N  E  R  G  A  P  Y  F  S  Q  A  P  F  S  G  K  I  W  134

401 GGCTGTCTATCAGCCACACCGATCAGTTGTGACAGCCAGTGTCATTTTGGAGGAAAATCATGAAAGCTAG   471  SEQ ID NO: 1
    CCGACAGATAGTCGGTGTGGCTAGTCAAACACTGTCGGTCACAGTAAAACCTCCTTTAGTACTTTCGATC        SEQ ID NO: 11

135 L  S  I  S  H  T  D  Q  F  V  T  A  S  V  I  L  E  E  N  H  E  S  *     156  SEQ ID NO: 2
```

FIG. 1

```
  1 ATGATTTACGGCATTGGGCTGGACATTACCGAGCTTAAACGGATCGCCTCTATGGCTGGGCGCCAGAAAAGGTTTGCCGAGCGGATTTTGACGCGAAGCG 100
    TACTAAATGCCGTAACCCGACCTGTAATGGCTCGAATTTGCCTAGCGGAGATACCGACCCGCGGTCTTTTCCAAACGGCTCGCCTAAAACTGCGCTTCGC
  1 M  I  Y  G  I  G  L  D  I  T  E  L  K  R  I  A  S  M  A  G  R  Q  K  R  F  A  E  R  I  L  T  R  S  E   34

101 AGCTTGACCAATACTACTATGAGCTTTCAGAGAAAAGAAAAAACGAATTTCTCGGGGCAGATTCGCGGGCAAAGAAGCGTTCTCGAAAGCATTTGGCACCGG 200
    TCGAACTGGTTATGATGATACTCGAAAGTCTCTTTTCTTTTTTGCTTAAAGAGCCCCGTCTAAGCGCCCGTTTCTTCGCAAGAGCTTTCGTAAACCGTGGCC
 35 S  L  D  Q  Y  Y  E  L  S  E  K  R  K  N  E  F  L  A  G  R  F  A  A  K  E  A  F  S  K  A  F  G  T  G   67

201 CATTGGGAGGCAGCTTCAGGACTTCGAGTCCGTCGAAGTCCTGTAACTTTAATCCTTTCGGTTTTACCGTTGACTGAACATGCTTGACTCGTCCGGCGCCAAGTG 300
    GTAACCCTCCGTCGAAGTCCTGAAGCTCAGGCAGCTTCAGGACATTGAAATTAGGAAGACCAAAATGGCAAGCCCTATATCATTTGTACGAAACTGACTTGACTGAACATGCTTGACTCGTCCGGCGCCAAGTG
 68 I  G  R  Q  L  S  F  Q  D  I  E  I  R  K  D  Q  N  G  K  P  Y  I  I  C  T  K  L  S  Q  A  A  V  H  100

301 GTATCGATCACTCATACAAAGAATACGCTGCCGCCGCAGGTTGTGATTGAAAGGTTGTCAAGCTAG 366    SEQ ID NO: 3
    CATAGCTAGTGAGTATGTTTCTTATGCGACGGCGGCGTCCAACACTAACTTTCCAACAGTTCGATC        SEQ ID NO: 12
101 V  S  I  T  H  T  K  E  Y  A  A  A  Q  V  V  I  E  R  L  S  S  *  121    SEQ ID NO: 4
```

USE OF S-YDCB AND B-YDCB, ESSENTIAL BACTERIAL GENES

FIELD OF THE INVENTION

The invention relates to the use of S-ydcB and B-ydcB, which are essential bacterial genes useful for identifying antibacterial agents.

BACKGROUND OF THE INVENTION

Bacterial infections may be cutaneous, subcutaneous, or systemic. Opportunistic bacterial infections proliferate, especially in patients afflicted with AIDS or other diseases that compromise the immune system. Most bacteria that are pathogenic to humans are gram positive bacteria. The bacterium *Streptococcus pneumoniae*, for example, typically infects the respiratory tract and can cause lobar pneumonia, as well as meningitis, sinusitis, and other infections.

SUMMARY OF THE INVENTION

The invention is based on the discovery that the S-ydcB gene in the gram positive bacterium *Streptococcus pneumoniae* and the B-ydcB gene in *Bacillus subtilis* are essential for survival. These genes are considered "essential" genes, and the S-ydcB and B-ydcB polypeptides are considered "essential" polypeptides. The invention features methods for using these genes and polypeptides to identify antibacterial compounds that inhibit a wide variety of bacteria (e.g., gram-positive and gram-negative bacteria, such as Streptococcus, Bacillus, and *E. coli*). Such inhibitors attenuate bacterial growth by inhibiting the activity of an S-ydcB or B-ydcB polypeptide (or homolog or ortholog thereof), or by inhibiting transcription of an S-ydcB or B-ydcB gene (or homolog or ortholog), or by inhibiting translation of the mRNA transcribed from an S-ydcB or B-ydcB gene (or homolog or ortholog). The S-ydcB and B-ydcB genes and polypeptides also are included within the invention and can be used in methods for identifying homologous genes and polypeptides in other bacterial strains.

The amino acid and nucleic acid sequences of S-ydcB are set forth in FIG. 1 as SEQ ID NOs:2 and 1, respectively. The amino acid and nucleic acid sequences of B-ydcB are set forth in FIG. 2 as SEQ ID NOs:4 and 3 respectively.

Now that the S-ydcB and B-ydcB genes described herein have been identified and shown to be essential for survival, these genes and polypeptides and their homologs can be used to identify antibacterial agents. "Homologs" are structurally similar genes contained within a species, while "orthologs" are functionally equivalent genes in other species. The identified antibacterial agents can readily be identified with high throughput assays to detect inhibition of the S-ydcB or B-ydcB polypeptide, or essential polypeptides with which S-ydcB and B-ydcB associate (e.g., in a pathway). This inhibition can be caused by small molecules interacting with (e.g., binding directly or indirectly to) the S-ydcB or B-ydcB polypeptide or other essential polypeptides in that pathway.

In an exemplary assay, but not the only assay, a promoter that responds to depletion of the B-ydcB or S-ydcB polypeptide (or homolog thereof) by upregulation or downregulation is linked to. a reporter gene. To identify a promoter that is up- or down-regulated by the depletion of a B-ydcB or S-ydcB protein, the gene encoding the B-ydcB or S-ydcB protein is deleted from the genome and replaced with a version of the gene in which the sequence encoding the B-ydcB or S-ydcB protein is operably linked to a regulatable promoter. The cells containing this regulatable genetic construct are kept alive by the B-ydcB or S-ydcB polypeptide produced from the genetic construct containing the regulatable promoter. However, the regulatable promoter allows expression of the B-ydcB or S-ydcB polypeptide to be reduced to a level that causes growth inhibition. Total RNA prepared from bacteria under such growth-limiting conditions is compared with RNA from wild-type cells. Standard methods of transcriptional profiling can be used to identify mRNA species that are either more or less abundant (i.e., up- or down-regulated) when expressed under the limiting conditions. Genomic sequence information, e.g., from GenBank, can be used to identify the promoter that drives expression of the identified RNA species. Such promoters are up- or down-regulated by depletion of the B-ydcB or S-ydcB polypeptide.

Having identified a promoter(s) that is up- or down-regulated by depletion of a B-ydcB or S-ydcB polypeptide, the promoter(s) is operably linked to a reporter gene (e.g., β-galactosidase, gus, or green fluorescent protein (GFP)). A bacterial strain containing this reporter gene construct is then exposed to test compounds. Compounds that inhibit the B-ydcB or S-ydcB polypeptide (or other polypeptides in an essential pathway in which the B-ydcB or S-ydcB polypeptide participates) will cause a functional depletion of the B-ydcB or S-ydcB polypeptide and therefore lead to an upregulation or downregulation of expression of the reporter gene. Because the polypeptides described herein are essential for the survival of bacteria, compounds that inhibit the B-ydcB or S-ydcB polypeptides in such an assay are expected to be antibacterial and can be further tested, if desired, in standard susceptibility assays.

Another suitable method for identifying antibacterial compounds involves screening for small molecules that specifically interact with (i.e., bind directly or indirectly to) the B-ydcB or S-ydcB polypeptide. A variety of suitable interaction and binding assays are known in the art as described, for example, in U.S. Pat. Nos. 5,585,277 and 5,679,582, incorporated herein by reference. For example, in various conventional assays, test compounds can be assayed for their ability to interact with a B-ydcB or S-ydcB polypeptide by measuring the ability of the small molecule to stabilize the B-ydcB or S-ydcB polypeptide in its folded, rather than unfolded, state. More specifically, one can measure the degree of protection from unfolding that is afforded by the test compound. Test compounds that bind the polypeptide with high affinity cause, for example, a large shift in the temperature at which the polypeptide is denatured. Test compounds that stabilize the B-ydcB or S-ydcB polypeptide in a folded state can be further tested for antibacterial activity in a standard susceptibility assay.

In a related method for identifying antibacterial compounds, the B-ydcB or S-ydcB polypeptide is used to isolate peptide or nucleic acid ligands that specifically bind the B-ydcB or S-ydcB polypeptide. These peptide or nucleic acid ligands are then used in a displacement screen to identify small molecules that interact with the B-ydcB or S-ydcB polypeptide. Such assays can be carried out essentially as described above.

Another suitable method for identifying inhibitors of the B-ydcB or S-ydcB polypeptide involves identifying a biochemical activity of the polypeptide and then screening for small molecule inhibitors of the activity using, for example, a high throughput screening method. S-ydcB and B-ydcB catalyze a reaction of CoenzymeA plus apo-Acyl Carrier Protein to produce holo-Acyl Carrier Protein and 3',5'-ADP (PAP). Based on this activity, various biochemical assays can be set up as high throughput screens to detect compounds that inhibit the enzymatic activity of ydcB. For example, incorporation of a labelled :version of CoenzymeA into the holoACP protein can readily :be detected. The label can be fluorescent, radioactive, or any easily detectable moiety, such as biotin. The holo-ACP protein can be the Acyl Carrier Protein derived from; any of a wide variety of bacteria, or it can be a peptide fragment thereof or a fusion portein containing ACP sequences. In an alternative assay, the production of PAP from the catalytic reaction described above is detected. PAP can be detected in a calorimetric assay in which sulfotransferase uses PAP as a cofactor (Lin et al., Analytical Biochemistry).

The various B-ydcB and S-ydcB polypeptides can be used, separately or together, in assays to identify test compounds that interact with these polypeptides. Test compounds that interact with these polypeptides then can readily be tested, in conventional assays, for their ability to inhibit bacterial growth. Test compounds that interact with the B-ydcB or S-ydcB polypeptides are candidate antibacterial agents, in contrast to compounds that do not interact with the B-ydcB or S-ydcB polypeptides. As described herein, any of a variety of art-known methods can be used to assay for the interaction of test compounds with the B-ydcB and S-ydcB polypeptides.

The invention also includes a method for identifying an antibacterial agent where the method entails: (a) contacting an S-ydcB or B-ydcB polypeptide, or homolog thereof, with a test compound; (b) detecting binding of the test compound to the polypeptide or homolog; and, optionally, (c) determining whether a test compound that binds to the polypeptide or homolog inhibits growth of bacteria, relative to growth of bacteria cultured in the absence of the test compound that binds to the polypeptide or homolog, as an indication that the test compound is an antibacterial agent.

In still another method, interaction of a test compound with an S-ydcB or B-ydcB polypeptide (e.g., binding) can be detected in a conventional two-hybrid system for detecting protein/protein interactions (e.g., in yeast or mammalian cells). A test compound found to interact with the S-ydcB or B-ydcB polypeptide can be further tested for antibacterial activity in a conventional susceptibility assay. Generally, in such two-hybrid methods, (a) the S-ydcB or B-ydcB polypeptide is provided as a fusion protein that includes the S-ydcB or:B-ydcB polypeptide fused to (i) a transcription activation domain of a transcription factor or (ii) a DNA-binding domain of a transcription factor; (b) the test polypeptide is provided as a fusion protein that includes the test polypeptide fused to (i) a transcription activation domain of a transcription factor or (ii) a DNA-binding domain of a transcription factor; and (c) binding of the test polypeptide to the S-ydcB or B-ydcB polypeptide is detected as a reconstitution of a transcription factor. Homologs of the S-ydcB and B-ydcB polypeptides can be used in similar methods. Reconstitution of the transcription factor can be detected, for example, by detecting transcription of a gene that is operably linked to a DNA sequence bound by the DNA-binding domain of the reconstituted transcription factor (See, for example, White, 1996, Proc. Natl. Acad. Sci. 93:10001–10003 and references cited therein and Vidal et al., 1996, Proc. Natl. Acad. Sci. 93:10315–10320).

In an alternative method, an isolated nucleic acid molecule encoding an S-ydcB or B-ydcB polypeptide is used to identify a compound that decreases the expression of a B-ydcB or S-ydcB polypeptide in vivo. Such compounds can be used as antibacterial agents. To discover such compounds, cells that express an S-ydcB or B-ydcB polypeptide are cultured, exposed to a test compound (or a mixture of test compounds), and the level of expression or activity is compared with the level of S-ydcB or B-ydcB polypeptide expression or activity in cells that are otherwise identical but that have not been exposed to the test compound(s) Many standard quantitative assays of gene expression can be utilized in this aspect of the invention.

To identify compounds that modulate expression of an S-ydcB or B-ydcB polypeptide (or homologous sequence), the test compound(s) can be added at varying concentrations to the culture medium of cells that express a S-ydcB or B-ydcB polypeptide (or homolog), as described herein. Such test compounds can include small molecules (typically, non-protein, non-polysaccharide chemical entities), polypeptides, and nucleic acids. The expression of the S-ydcB or B-ydcB polypeptide is then measured, for example, by Northern blot PCR analysis or RNAse protection analyses using a nucleic acid molecule of the invention as a probe. The level of expression in the presence of the test molecule, compared with the level of expression in its absence, will indicate whether or not the test molecule alters the expression of the S-ydcB or B-ydcB polypeptide. Because the S-ydcB and B-ydcB polypeptides, and homologs thereof, are essential for survival, test compounds that inhibit the expression and/or function of the B-ydcB or S-ydcB polypeptide will inhibit growth of, or kill, the cells that express B-ydcB or S-ydcB polypeptides.

Typically, the test compound will be a small organic molecule. Alternatively, the test compound can be a test polypeptide (e.g., a polypeptide having a random or predetermined amino acid sequence; or a naturally-occurring or synthetic polypeptide) or a nucleic acid, such as a DNA or RNA molecule. The test compound can be a naturally-occurring compound or it can be synthetically produced, if desired. Synthetic libraries, chemical libraries, and the like can be screened to identify compounds that bind the S-ydcB or B-ydcB polypeptide. More generally, binding of test a compound to the S-ydcB or B-ydcB polypeptide or homolog can be detected either in vitro or in vivo. If desired, the above-described methods for identifying compounds that modulate the expression of the polypeptides of the invention can be combined with measuring the levels of the S-ydcB or B-ydcB polypeptides expressed in the cells, e.g., by performing a Western blot analysis using antibodies that bind an S-ydcB or B-ydcB polypeptide.

Regardless of the source of the test compound, the B-ydcB and S-ydcB polypeptides described herein can be used to identify compounds that inhibit the activity of an S-ydcB or B-ydcB protein or transcription of an S-ydcB or B-ydcB gene, or translation of the mRNA transcribed from such a gene. These antibacterial agents can be used to inhibit a wide spectrum of pathogenic or non-pathogenic bacterial strains, particularly gram-positive bacteria.

In other embodiments, the invention includes pharmaceutical formulations that include a pharmaceutically acceptable excipient and an antibacterial agent identified using the methods described herein. In particular, the invention includes pharmaceutical formulations that contain antibacterial agents that inhibit the growth of, or kill, pathogenic bacterial strains (e.g., pathogenic gram positive bacterial strains such as pathogenic Streptococcus strains). Such pharmaceutical formulations can be used in a method of treating a bacterial infection in an organism (e.g., a Streptococcus infection). Such a method entails administering to the organism a therapeutically effective amount of the pharmaceutical formulation, i.e., an amount sufficient to ameliorate signs and/or symptoms of the bacterial infection. In particular, such pharmaceutical formulations can be used to treat bacterial infections in mammals such as humans and domesticated mammals (e.g., cows, pigs, dogs, and cats), and in plants. The efficacy of such antibacterial agents in humans can be estimated in an animal model system well known to those of skill in the art (e.g., mouse and rabbit model systems of, for example, streptococcal pneumonia).

The invention further features methods of identifying from a large group of mutants those strains that have conditional lethal mutations. In general, the gene and corresponding gene product are subsequently identified, although the strains themselves can be used in screening or diagnostic assays. The mechanism(s) of action for the identified genes and gene products provide a rational basis for the design of antibacterial therapeutic agents. These antibacterial agents reduce the action of the gene product in a wild type strain, and therefore are useful in treating a subject with that type, or a similarly susceptible type, of infection by administering the agent to the subject in a pharmaceutically effective amount. Reduction in the action of the gene product includes competitive inhibition of the gene product for the active site of an enzyme or receptor; non-competitive inhibition; disrupting an intracellular cascade path which requires the gene product; binding to the gene product itself, before or after post-translational processing; and acting as a gene product mimetic, thereby down-regulating the activity.

Furthermore, the presence of the gene sequence in certain cells (e.g., a pathogenic bacterium of the same genus or similar species), and the absence or divergence of the sequence in host cells can be determined, if desired. Therapeutic agents directed toward genes or gene products that are not present in the host have several advantages, including fewer side effects, and lower overall dosage.

The invention also features an isolated S-ydcB polypeptide having the amino acid sequence set forth in SEQ ID NO:2, as depicted in FIG. 1, or conservative variations 15 thereof. An isolated nucleic acid encoding S-ydcB also is included within the invention. In addition, the invention includes (a) an isolated nucleic acid having the sequence of SEQ ID NO:1, as depicted in FIG. 1, or degenerate variants thereof; (b) an isolated nucleic acid having the sequence of SEQ ID NO:1, or degenerate variants thereof, wherein T is replaced by U; (c) nucleic acids complementary to (a) and (b); and (d) fragments of (a), (b), and (c) that are at least 15 base pairs in length and that hybridize under stringent conditions, as described below, to genomic DNA encoding the polypeptide of SEQ ID NO:2.

Identification of the S-ydcB gene allows homologs of the S-ydcB gene to be found in other strains within the species Streptococcus. The S-ydcB gene has an ortholog in *Bacillus subtilis*, termed "B-ydcB," the amino acid and nucleic acid sequences of which are set forth in FIG. 2 (SEQ ID NOs:4 and 3,; respectively). The B-ydcB gene and polypeptide also can be used to identify compounds that inhibit bacterial growth (e.g., compounds that inhibit the activity of an S-ydcB or B-ydcB protein (or homolog or ortholog), or inhibit transcription of an S-ydcB or B-ydcB gene (or homolog or ortholog thereof)).

The S-ydcB polypeptides and genes described herein include the polypeptide and gene set forth in FIG. 1 herein, as well as isozymes, variants, and conservative variations of the sequences set forth in FIG. 1. The invention includes various isozymes of S-ydcB. For example, the invention includes a gene that encodes a S-ydcB polypeptide but which gene includes one or more point mutations, deletions, or promoter variants, provided that the resulting polypeptide retains a biological function of a S-ydcB polypeptide. The S-ydcB polypeptide has structural characteristics of acyl carrier protein synthase and displays such synthase activity in vitro. Thus, the various isozymes, variants, and conservative variations of the S-ydcB sequences set forth in FIG. 1 retain a biological function of S-ydcB as determined, for example, in an assay of acyl carrier synthase activity (e.g., as described above) or in a conventional complementation assay or binding assay. Also encompassed by the term S-ydcB gene are degenerate variants of the nucleic acid sequences set forth in FIG. 1 (SEQ ID NO:1). Degenerate variants of a nucleic acid sequence exist because of the degeneracy of the amino acid code; thus, those sequences that vary from the sequence represented by SEQ ID NO:1, but which nonetheless encode a polypeptide are included within the invention.

Likewise, because of the similarity in the structures of amino acids, conservative variations (as described herein) can be made in the amino acid sequence of the S-ydcB polypeptide while retaining the function of the polypeptide (e.g., as determined in a conventional complementation or binding assay). Other S-ydcB polypeptides and genes identified may be such conservative variations or degenerate variants of the particular S-ydcB polypeptide and nucleic acid set forth in FIG. 1 (SEQ ID Nos:1 and 2). Polypeptides that are substantially identical to the S-ydcB polypeptide and gene share at least 70%, e.g., 80% or 90%, sequence identity with SEQ ID Nos:2 and 1, respectively. Irrespective of the percent sequence identity between the S-ydcB sequence and the sequences represented by SEQ ID Nos:2 and 1, the S-ydcB genes and polypeptides encompassed by the invention preferably are able to complement for the lack of S-ydcB function (e.g., in a temperature-sensitive mutant) in a standard complementation assay. As described above for S-ydcB, the invention also includes various isozymes, variants, conservative variations and the like of the *B. subtilis* B-ydcB nucleic acid and polypeptide, which also has structural characteristics of acyl carrier protein synthases.

In various embodiments, the homologs or orthologs of the S-ydcB polypeptide used in the assays described herein is derived from a non-pathogenic or pathogenic gram positive bacterium.

The invention offers several advantages. For example, the methods for identifying antibacterial agents can be configured for high throughput screening of numerous candidate antibacterial agents. Because the B-ydcB and S-ydcB genes disclosed herein are thought to be highly conserved, antibacterial drugs targeted to these genes or their gene products are expected to have a broad spectrum of antibacterial activity.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described herein. All publications, patent applications, patents, and other references mentioned herein are incorporated herein by reference in their entirety. In the case of a conflict, the present specification, including definitions, will control. In addition, the materials, methods, and examples are illustrative and are not intended to limit the scope of the invention, which is defined by the claims.

Other features and advantages of the invention will be apparent from the following detailed description, and from the claims.

BRIEF DESCRIPTION OF THE DRAWINGS

FIG. 1 is a listing of the amino acid and nucleic acid sequences of the S-ydcB polypeptide and the coding strand of the gene from a *Streptococcus pneumoniae* strain (SEQ ID NOs:2 and 1, respectively). The non-coding strand is set forth as SEQ ID NO:11.

FIG. 2 is a listing of the full-length amino acid and nucleic acid sequences of the B-ydcB polypeptide and the coding strand of the gene from a *B. subtilis* strain (SEQ ID NOs:4 and 3, respectively). The non-coding strand is set forth as SEQ ID NO:12.

DETAILED DESCRIPTION OF THE INVENTION

Figure 3:
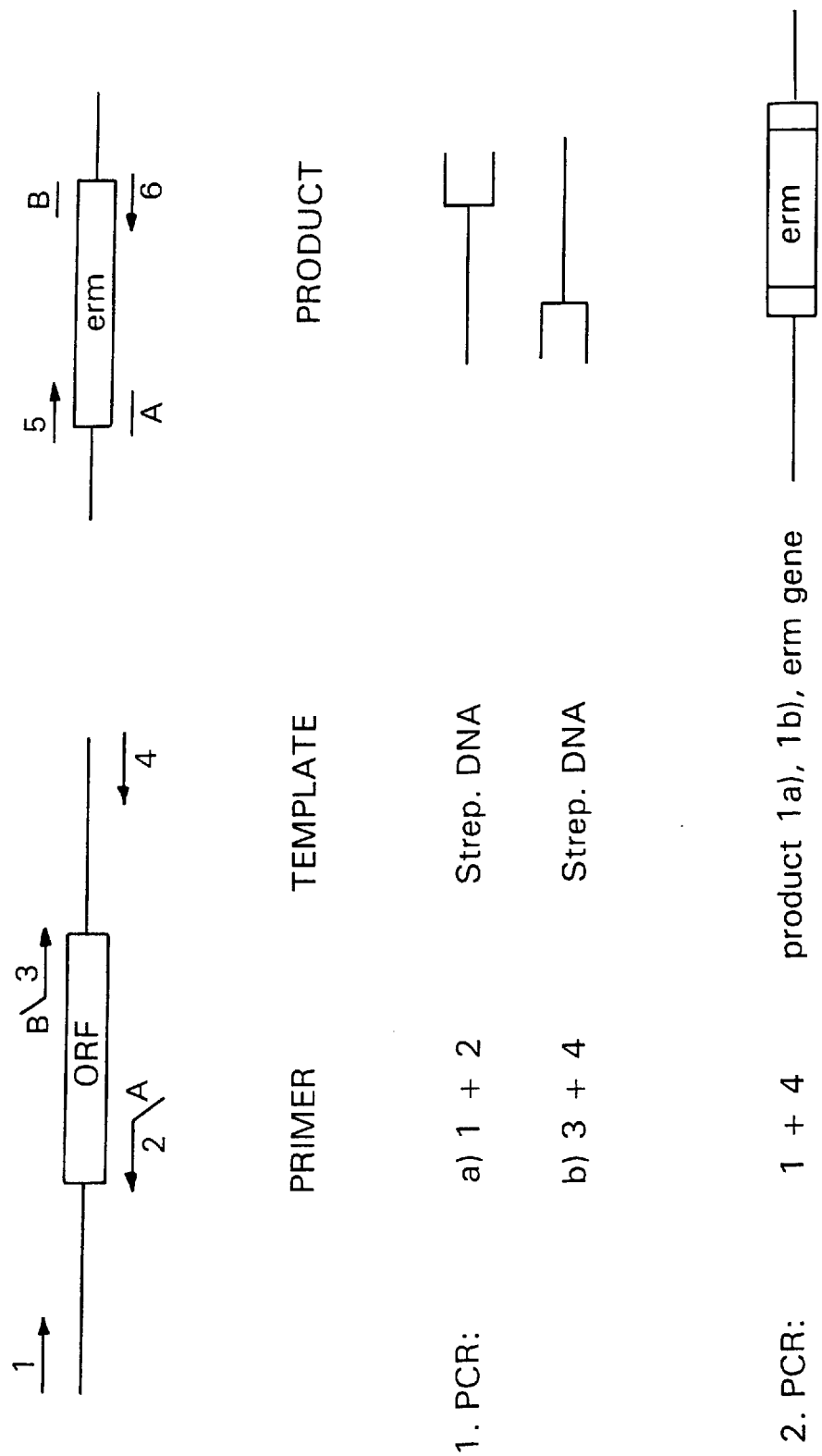
FIG. 3 is a schematic representation of the PCR strategy used to produce DNA molecules used for targeted deletions of essential genes in *Streptococcus pneumoniae*.

The invention features methods for using the genes S-ydcB and B-ydcB, or homologs or orthologs thereof, to identify antibacterial compounds that inhibit a wide variety of bacteria. The amino acid and nucleic acid sequences of S-ydcB and B-ydcB are set forth in FIGS. 1 and 2.

Nucleic acids of the invention include both RNA and DNA, including genomic DNA and synthetic (e.g., chemically synthesized) DNA. Nucleic acids can be double-stranded or single-stranded. Where single-stranded, the nucleic acid may be a sense strand or an antisense strand. Nucleic acids can be synthesized using oligonucleotide analogs or derivatives (e.g., inosine or phosphorothioate nucleotides). Such oligonucleotides can be used, for example, to prepare nucleic acids that have altered base-pairing abilities or increased resistance to nucleases.

An isolated nucleic acid is a DNA or RNA that is not immediately contiguous with both of the coding sequences with which it is immediately contiguous (one on the 5' end and one on the 3' end) in the naturally occurring genome of the organism from which it is derived. Thus, in one embodiment, an isolated nucleic acid includes some or all of the 5' non-coding (e.g., promoter) sequences that are immediately contiguous to the coding sequence. The term therefore includes, for example, a recombinant DNA that is incorporated into a vector, into an autonomously replicating plasmid or virus, or into the genomic DNA of a prokaryote or eukaryote, or which exists as a separate molecule (e.g., a genomic DNA fragment produced by PCR or restriction endonuclease treatment) independent of other sequences. It also includes a recombinant DNA that is part of a hybrid gene encoding an additional polypeptide sequence. The term "isolated" can refer to a nucleic acid or polypeptide that is substantially free of cellular material, viral material, or culture medium (when produced by recombinant DNA techniques), or chemical precursors or other chemicals (when chemically synthesized). Moreover, an isolated nucleic acid fragment is a nucleic acid fragment that is not naturally occurring as a fragment and would not be found in the natural state.

A nucleic acid sequence that is substantially identical to an S-ydcB nucleotide sequence is at least 80% identical to the nucleotide sequence of S-ydcB as represented by SEQ ID NO:1, as depicted in FIG. 1. For purposes of comparison of nucleic acids, the length of the reference nucleic acid sequence will generally be at least 40 nucleotides, e.g., at least 60 nucleotides or more nucleotides.

To determine the percent identity of two amino acid sequences or of two nucleic acids, the sequences are aligned for optimal comparison purposes (e.g., gaps can be introduced in the sequence of a first amino acid or nucleic acid sequence for optimal alignment with a second amino or nucleic acid sequence). The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position. The percent identity between the two sequences is a function of the number of identical positions shared by the sequences (i.e., % identity=# of identical positions/total # of overlapping positions×100). Preferably, the two sequences are the same length.

The determination of percent identity or homology between two sequences can be accomplished using a mathematical algorithm. A suitable, mathematical algorithm utilized for the comparison of two sequences is the algorithm of Karlin and Altschul (1990) *Proc. Nat'l Acad. Sci. USA* 87:2264–2268, modified as in Karlin and Altschul (1993) *Proc. Nat'l Acad. Sci. USA* 90:5873–5877. Such an algorithm is incorporated into the NBLAST and XBLAST programs of Altschul, et al. (1990) *J. Mol. Biol.* 215:403–410. BLAST nucleotide searches can be performed with the NBLAST program, score=100, wordlength=12 to obtain nucleotide sequences homologous to the nucleic acid molecules of the invention. BLAST protein searches can be performed with the XBLAST program, score=50, wordlength=3 to obtain amino acid sequences homologous to the protein molecules of the invention. To obtain gapped alignments for comparison purposes, Gapped BLAST can be utilized as described in Altschul et al., (1997) *Nucleic Acids Res.* 25:3389–3402. When utilizing BLAST and Gapped BLAST programs, the default parameters of the respective programs (e.g., XBLAST and NBLAST) can be used. See http://www.ncbi.nlm.nih.gov. Another example of a mathematical algorithm utilized for the comparison of sequences is the algorithm of Myers and Miller, CABIOS (1989). Such an algorithm is incorporated into the ALIGN program (version 2.0) which is part of the GCG sequence alignment software package. When utilizing the ALIGN program for comparing amino acid sequences, a PAM120 weight residue table, a gap length penalty of 12, and a gap penalty of 4 can be used.

The percent identity between two sequences can be determined using techniques similar to those described above, with or without allowing gaps. In calculating percent identity, only exact matches are counted.

The B-ydcB and S-ydcB polypeptides useful in practicing the invention include, but are not limited to, recombinant polypeptides and natural polypeptides. Also useful in the invention are nucleic acid sequences that encode forms of the B-ydcB or S-ydcB polypeptides in which naturally occurring amino acid sequences are altered or deleted. Preferred nucleic acids encode polypeptides that are soluble under normal physiological conditions. Also within the invention are nucleic acids encoding fusion proteins in which a portion of a B-ydcB or S-ydcB polypeptide is fused to an unrelated polypeptide (e.g., a marker polypeptide or a fusion partner) to create a fusion protein. For example, the polypeptide can be fused to a hexa-histidine tag to facilitate purification of bacterially expressed polypeptides, or to a hemagglutinin tag to facilitate purification of polypeptides expressed in eukaryotic cells. The invention also includes, for example, isolated polypeptides (and the nucleic acids that encode these polypeptides) that include a first portion and a second portion; the first portion includes, e.g., a B-ydcB or S-ydcB polypeptide, and the second portion includes an immunoglobulin constant (Fc) region or a detectable marker.

The fusion partner can be, for example, a polypeptide which facilitates secretion, e.g., a secretory sequence. Such a fused polypeptide is typically referred to as a preprotein. The secretory sequence can be cleaved by the host cell to form the mature protein. Also within the invention are nucleic acids that encode a B-ydcB or S-ydcB polypeptide fused to a polypeptide sequence to produce an inactive preprotein. Preproteins can be converted into the active form of the protein by removal of the inactivating sequence.

The invention also includes nucleic acids that hybridize, e.g., under moderate or highly stringent hybridization conditions (as defined herein) to all or a portion of the nucleotide sequences represented by SEQ ID NO:1 or 3, or their complements. The hybridizing portion of the hybridizing nucleic acids is typically at least 15 (e.g., 20, 25, 30, or 50) nucleotides in length. The hybridizing portion of the hybridizing nucleic acid is at least 80%, e.g., at least 95%, or at least 98%, identical to the sequence of a portion or all of a nucleic acid encoding a B-ydcB or S-ydcB polypeptide or its complement. Hybridizing nucleic acids of the type described herein can be used as a cloning probe, a primer (e.g., a PCR primer), or a diagnostic probe. Nucleic acids that hybridize to the nucleotide sequences represented by SEQ ID NO:1 and 3 are considered "antisense oligonucleotides."

Also included in the invention are various engineered cells, e.g., transformed host cells, that contain a ydcB nucleic acid described herein. A transformed cell is a cell into which (or into an ancestor of which) has been introduced, by means of recombinant DNA techniques, a nucleic acid encoding a ydcB; polypeptide. Both prokaryotic and eukaryotic cells are included, e.g., bacteria, such as Streptococcus, Bacillus, and the like.

Also within in the invention are genetic constructs (e.g., vectors and plasmids) that include a nucleic acid of the invention which is operably linked to a transcription and/or translation sequence to enable expression, e.g., expression vectors. A selected nucleic acid, e.g., a DNA molecule encoding a ydcB polypeptide, is "operably linked" to a transcription and/or translation sequence when it is positioned adjacent to one or more sequence elements, e.g., a promoter, which direct transcription and/or translation of the sequence such that the sequence elements can control transcription and/or translation of the selected nucleic acid.

The invention also features purified or isolated polypeptides encoded by the B-ydcB and S-ydcB genes. The terms "protein" and "polypeptide" both refer to any chain of amino acids, regardless of length or post-translational modification (e.g., glycosylation or phosphorylation). Thus, the terms B-ydcB polypeptide and S-ydcB polypeptide include full-length, naturally occurring, isolated B-ydcB and S-ydcB proteins, respectively, as well as recombinantly or synthetically produced polypeptides that correspond to the full-length, naturally occurring proteins, or to a portion of the naturally occurring or synthetic polypeptides.

A purified or isolated compound is a composition that is at least 60% by weight the compound of interest, e.g., a B-ydcB polypeptide. Preferably the preparation is at least 75% (e.g., at least 90%, 95%, or even 99%) by weight the compound of interest. Purity can be measured by any appropriate standard method, e.g., column chromatography, polyacrylamide gel electrophoresis, or HPLC analysis.

Preferred S-ydcB polypeptides include a sequence substantially identical to all or a portion of a naturally occurring S-ydcB polypeptide, e.g., including all or a portion of the sequence shown in FIG. 1. Preferred B-ydcB polypeptides include a sequence substantially identical to all or a portion of a naturally occurring B-ydcB polypeptide, e.g., including all or a portion of the sequence shown in FIG. 2. Polypeptides "substantially identical" to the B-ydcB polypeptide or S-ydcB polypeptide sequences described herein have an amino acid sequence that is at least 80% identical to the amino acid sequence of the B-ydcB polypeptide or S-ydcB polypeptide represented by SEQ ID NOs:2 and 4 (measured as:described herein). The new polypeptides can also have a greater percentage identity, e.g., 85%, 90%, 95%, or even higher. For purposes of comparison, the length of the reference polypeptide sequence will generally be at least 16 amino acids, e.g., at least 20 or 25 amino acids.

In the case of polypeptide sequences that are less than 100% identical to a reference sequence, the non-identical positions are preferably, but not necessarily, conservative substitutions for the reference sequence. Conservative substitutions typically include substitutions within the following groups: glycine and alanine; valine, isoleucine, and leucine; aspartic acid and glutamic acid; asparagine and glutamine; serine and threonine; lysine and arginine; and phenylalanine and tyrosine.

Where a particular polypeptide is said to have a specific percent identity to a reference polypeptide of a defined length, the percent identity is relative to the reference polypeptide. Thus, a polypeptide that is 50% identical to a reference polypeptide that is 100 amino acids long can be a 50 amino acid polypeptide that is completely identical to a 50 amino acid long portion of the reference polypeptide. Alternatively, it can be a 100 amino acid long polypeptide that is 50% identical to the reference polypeptide over its entire:length. Of course, other polypeptides also will meet the same criteria.

Also encompassed by the invention is a method of obtaining a gene homologous to a B-ydcB or S-ydcB gene. Such a method entails obtaining a labeled probe that includes an isolated nucleic acid which encodes all or a portion of a B-ydcB or S-ydcB nucleic acid, or a homolog thereof; screening a nucleic acid fragment library with the labeled probe under conditions that allow hybridization of the probe to nucleic acid fragments in the library, thereby forming nucleic acid duplexes; isolating labeled duplexes, if any; and preparing a full-length gene sequence from the nucleic acid fragments in any labeled duplex to obtain a gene related to the B-ydcB or S-ydcB genes.

Identifying Essential Streptococcus Genes

As shown by the experiments described below, the B-ydcB and S-ydcB genes are essential for survival of *Streptococcus pneumoniae*. *Streptococcus pneumoniae* is available from the ATCC. In general, and for the examples set forth below, essential genes can be identified by creating targeted deletions of genes of interest in a bacterium, e.g., *S. pneumoniae*. The gene of interest was selected as follows. Using standard molecular biology techniques, a library containing fragments of the *Streptococcus pneumoniae* genome was made, using M13 phage or plasmid DNA as the vector. Open reading frames (ORFs) contained within this library were randomly sequenced, using primers that hybridized to the vector. The gene of interest selected for targeted deletion satisfied four criteria, as determined by comparing the sequences with the GenBank database of nucleotide sequences: (i) the ORF had no known function; (ii) the ORF had an ortholog in Bacillus subtilis; (iii) the ORF was conserved in other bacteria, with $p<10^{-10}$; and (iv) the ORF had no known eukaryotic ortholog, with $p>10^{-3}$. The Streptococcus gene S-ydcB met each of these criteria, suggesting that a compound that inhibited the S-ydcB gene or gene product would have a broad spectrum of antibacterial activity.

The S-ydcB gene was replaced with a nucleic acid sequence conferring resistance to the antibiotic erythromycin (an "erm" gene). Other genetic markers can be used in lieu of this particular antibiotic resistance marker. Polymerase chain reaction (PCR) amplification was used to make a targeted deletion in the Streptococcus genomic DNA, as shown in FIG. 3. Several PCR reactions were used to produce the DNA molecules needed to carry out target deletion of the genes of interest. First, using primers 5 and 6, an erm gene was amplified from pIL252 from B. subtilis (available from the Bacillus Genetic Stock Center, Columbus, Ohio). Primer 5 consists of 21 nucleotides that are identical to the promoter region of the erm gene and complementary to Sequence A. Primer 5 has the sequence 5'GTG TTC GTG CTG ACT TGC ACC3' (SEQ ID NO:5). Primer 6 consists of 21 nucleotides that are complementary to the 3' end of the erm gene. Primer 6 has the sequence .5'GAA TTA TTT CCT CCC GTT AAA3' (SEQ ID NO:6). PCR amplification of the erm gene was carried out under the following conditions: 30 cycles of 94° C. for 1 minute, 55° C. for 1 minute, and 72° C. for 1.5 minutes, followed by one cycle of 72° C. for 10 minutes.

In the second and third PCR reactions, sequences flanking the gene of interest were amplified and produced as hybrid DNA molecules that also contained a portion of the erm gene. The second reaction produced a double-stranded DNA molecule (termed "Left Flanking Molecule") that includes sequences upstream of the 5' end of the gene of interest and the first 21 nucleotides of the erm gene. As shown in FIG. 3, this reaction utilized primer 1, which is 21 nucleotides in length and identical to a sequence that is located approximately 500 bp upstream of the translation start site of the gene of interest. Primers 1 and 2 are gene-specific and include the sequences 5'TTA ACG CCA TCT ATG CTG CT3' (SEQ ID NO:7) and 5'TTC CGT GTC CAA CTA TCA TTC3' (SEQ ID NO:8), respectively, for S-ydcB. Primer 2 is 42 nucleotides in length, with 21 of the nucleotides at the 3' end of the primer being complementary to the 5' end of the sense strand of the gene of interest. The 21 nucleotides at the 5' end of the primer were identical to Sequence A and are therefore: complementary to the 5' end of the erm gene. Thus, PCR amplification using primers 1 and 2 produced the left flanking DNA molecule, which is a hybrid DNA molecule containing a sequence located upstream of the gene of interest and 21 base pairs of the erm gene, as shown in FIG. 3.

The third PCR reaction was similar to the second reaction, but produced the right flanking DNA molecule, shown in FIG. 3. The right flanking DNA molecule contains 21 base pairs of the 3' end of the erm gene, a 21 base pair portion of the 3' end of the gene of interest, and sequences downstream of the gene of interest. This right flanking DNA molecule was produced with gene-specific primers 3 and 4. For S-ydcB, primers 3 and 4 include the sequences 5'AGT TTG TGA CAG CCA GTG TCA3' (SEQ ID NO:9) and 5'TGA TTC CTC ATC AGC AGT AGC3' (SEQ ID NO:10), respectively. Primer 3 is 42 nucleotides; the 21 nucleotides at the 5' end of Primer 3 are identical to Sequence B and therefore are identical to the 3' end of the erm gene. The 21 nucleotides at the 3' end of Primer 3 are identical to the 3' end of the gene of interest. Primer 4 is 21 nucleotides in length and is complementary to a sequence located approximately 500 bp downstream of the gene of interest.

PCR amplification of the left and right flanking DNA molecules was carried out, separately, in 50 µl reaction mixtures containing: 1 µl Streptococcus pneumoniae (RX1) DNA (0.25 µg), 2.5 µl Primer 1 or Primer 4 (10 pmol/µl), 2.5 µl Primer 2 or Primer 3 (20 pmol/µl), 1.2 µl a mixture dNTPs (10 mM each), 37 µl $H_2O$, 0.7 µl Taq polymerase (5 U/µl), and 5 µl 10×Taq polymerase buffer (10 mM Tris, 50 mM KCl, 2.5 mM $MgCl_2$). The left and right flanking DNA molecules were amplified using the following PCR cycling program: 95° C. for 2 minutes; 72° C. for 1 minute; 94° C. for 30 seconds; 49° C. for 30 seconds; 72° C. for 1 minute; repeating the 94° C., 49° C., and 72° C. incubations 30 times; 72° C. for 10 minutes and then stopping the reactions. A 15 µl aliquot of each reaction mixture then was electrophoresed through a 1.2% low melting point agarose gel in TAE buffer and then stained with ethidium bromide. Fragments containing the amplified left and right flanking DNA molecules were excised from the gel and purified using the QIAQUICK™ gel extraction kit (Qiagen, Inc.) Other art-known methods for amplifying and isolating DNA can be substituted. The flanking left and right DNA fragments were eluted into 30 µl TE buffer at pH 8.0.

The amplified erm gene and left and right flanking DNA molecules were then fused together to produce the fusion product, as shown in FIG. 3. The fusion PCR reaction was carried out in a volume of 50 µl containing: 2 µl of each of the left and right flanking DNA molecules and the erm gene PCR product; 5 µl of 10×buffer; 2.5 µl of Primer 1 (10 pmol/µl); 2.5 µl of Primer 4 (10 pmol/µl), 1.2 µl dNTP mix (10 mM each) 32 µl $H_2O$, and 0.7 µl Taq polymerase. The PCR reaction was carried out using the following cycling program: 95° C. for 2 minutes; 72° C. for 1 minute; 94° C. for 30 seconds, 48° C. for 30 seconds; 72° C. for 3 minutes; repeat the 94° C., 48° C. and 72° C. incubations 25 times; 72° C. for 10 minutes. After the reaction was stopped, a 12 µl aliquot of the reaction mixture was electrophoresed through an agarose gel to confirm the presence of a final product of approximately 2 kb.

Figure 4:
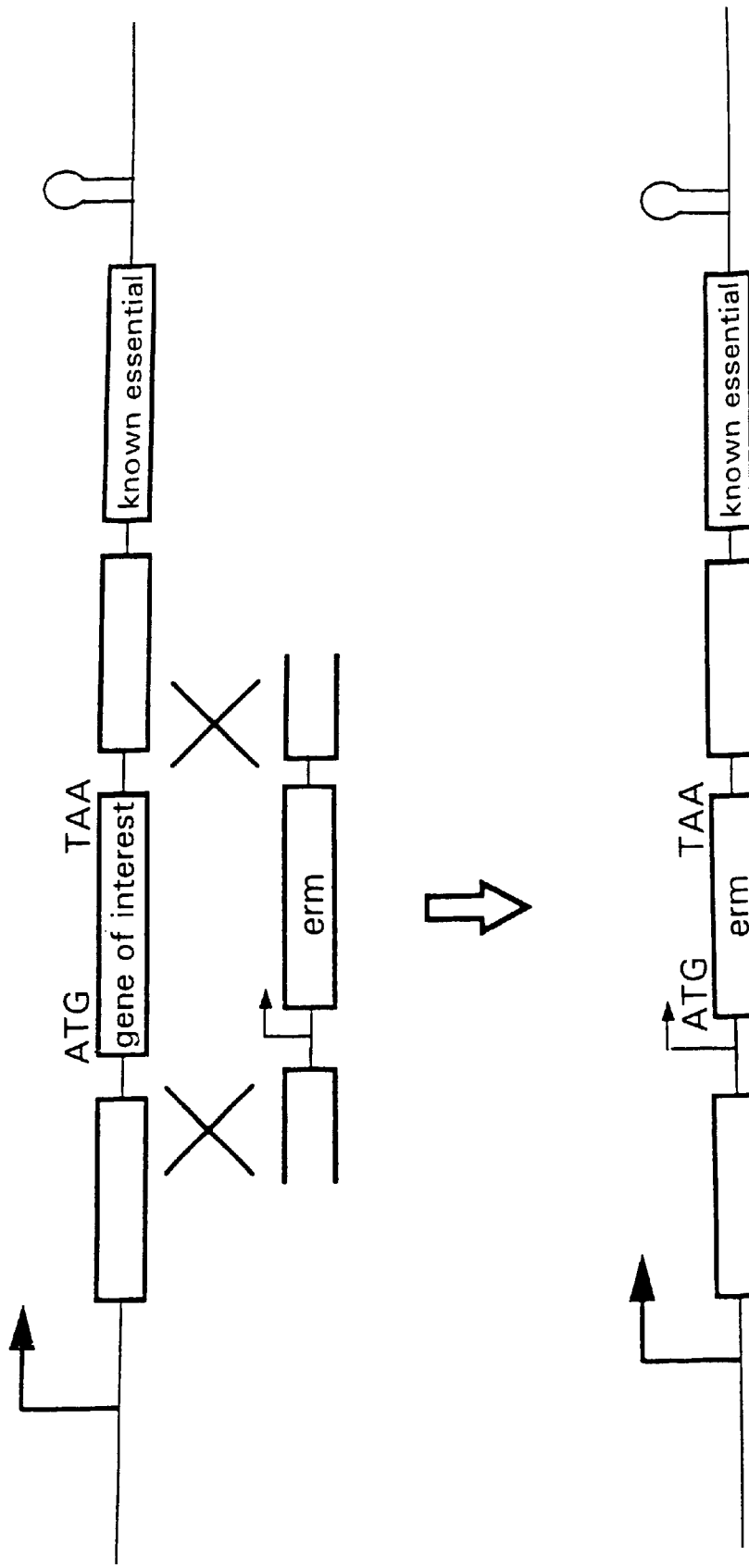
FIG. 4 is a schematic representation of the strategy used to produce targeted deletions of essential genes in *Streptococcus pneumoniae*.

A 5 µl aliquot of the fusion product was used to transform S. pneumoniae grown on a medium containing erythromycin in accordance with standard techniques. As shown in FIG. 4, the fusion product and the S. pneumoniae genome undergo a homologous recombination event so that the erm gene replaces the chromosomal copy of the gene of interest, thereby creating a gene knockout. Disruption of S-ydcB gene results in no growth on a medium containing erythromycin. Using this gene knockout method, the S-ydcB gene was identified as being essential for survival.

Identification of B-ydcB

Having shown that the S-ydcB gene is essential for survival of Streptococcus, it was used to identify an ortholog in B. subtilis, termed "B-ydcB," which is essential for survival of B. subtilis. The coding sequence of S-ydcB was used to search the GenBank database of nucleotide sequences, and an ortholog of the S-ydcB sequence was identified in B. subtilis. Sequence comparisons were performed using the Basic Local Alignment Search Tool (BLAST) (Altschul et al., J. Mol. Biol. 215:403–410, 1990). The percent sequence identity shared by the S-ydcB polypeptides and the B. subtilis ortholog, B-ydcB, was determined using the GAP program from the Genetics Computer Group (GCG) Wisconsin Sequence Analysis Package (Wisconsin Package Version 9.1; Madison, Wis.).

The default parameters for gap weight (12) and length weight (4) were used.

Generally, the S-ydcB and B-ydcB polypeptides and their homologs and orthologs share at least 25% (e.g., at least 30%, 35%, or 40%) sequence identity (S-ydcB and B-ydcB share 43% identity). Typically, the DNA sequences encoding S-ydcB and B-ydcB polypeptides and their homologs or orthologs share at least 20% (e.g., at least 30%, 35%, 40%, or 45%) sequence identity (S-ydcB and B-ydcB share 51%).

Bioinformatics analysis of the S-ydcB gene showed that this gene is widely conserved among bacteria. To confirm that the identified *B. subtilis* ortholog of S-ydcB is essential for survival, the orthologous gene was deleted from the *B. subtilis* genome. Such a deletion strain has been constructed and does not survive, confirming the essential nature of the polypeptide. The fact that the S-ydcB and B-ydcB genes are essential for survival suggests that antibacterial drugs targeted to these genes or their gene products are expected to have antibacterial activity in a broad spectrum bacteria containing related genes and gene products (e.g., pathogenic and non-pathogenic bacteria, particularly gram-positive bacteria).

Assay for Antibacterial Agents

The invention provides a method for identifying an antibacterial agent(s). Although the inventor is not bound by any particular theory as to the biological mechanism involved, the new antibacterial agents are thought to inhibit specifically (1) the function of the S-ydcB or B-ydcB polypeptides, or homologs or orthologs thereof, or (2) expression of the S-ydcB or B-ydcB genes, or homologs or orthologs thereof. In preferred methods, screening for antibacterial agents is accomplished by identifying those compounds (e.g., small organic molecules) that inhibit the activity of an S-ydcB or B-ydcB polypeptide or the expression of an S-ydcB or B-ydcB gene. Such antibacterial agents are expected to have a broad spectrum of antibacterial activity.

In an exemplary assay, but not the only assay, a promoter that responds to depletion of the B-ydcB or S-ydcB polypeptide by upregulation or downregulation is linked to a reporter gene (e.g., β-galactosidase, gus, or GFP), as described above. A bacterial strain containing this reporter gene construct is then exposed to test compounds. Compounds that inhibit the S-ydcB or B-ydcB polypeptide (or other polypeptides in an essential pathway in which the B-ydcB or S-ydcB polypeptide participates) will cause a functional depletion of the B-ydcB or S-ydcB polypeptide and therefore lead to an upregulation or downregulation of expression of the reporter gene. Because the polypeptides described herein are essential for the survival of bacteria, compounds that inhibit the S-ydcB or B-ydcB polypeptide in such an assay are expected to be antibacterial agents and can be further tested, if desired, in conventional susceptibility assays.

In other suitable methods, screening for antibacterial agents is accomplished by (i) identifying those compounds that interact with or bind to an S-ydcB or B-ydcB polypeptide and (ii) further testing such compounds for their ability to inhibit bacterial growth in vitro or in vivo.

Specific binding of a test compound to a polypeptide can be detected, for example, in vitro by reversibly or irreversibly immobilizing the test compound(s) on a substrate, e.g., the surface of a well of a 96-well polystyrene microtitre plate. Methods for immobilizing polypeptides and other small molecules are well known in the art. For example, the microtitre plates can be coated with s-ydcB or B-ydcB polypeptide(s) and/or homolog(s) by adding the polypeptide(s) in a solution (typically, at a concentration of 0.05 to 1 mg/ml in a volume of 1–100 µl) to each well, and incubating the plates at room temperature to 37° C. for 0.1 to 36 hours. Polypeptides that are not bound to the plate can be removed by shaking the excess solution from the plate, and then washing the plate (once or repeatedly) with water or a buffer. Typically, the polypeptide is in water or a buffer. The plate is then washed with a buffer that lacks the bound polypeptide. To block the free protein-binding sites on the plates, the plates are blocked with a protein that is unrelated to the bound polypeptide. For example, 300 µl of bovine serum albumin (BSA) at a concentration of 2 mg/ml in Tris-HCl is suitable. Suitable substrates include those substrates that contain a defined cross-linking chemistry (e.g., plastic substrates, such as polystyrene, styrene, or polypropylene substrates from Corning Costar Corp. (Cambridge, MA), for example). If desired, a beaded particle, e.g., beaded agarose or beaded sepharose, can be used as the substrate.

Interaction of the test compound with a B-ydcB or S-ydcB polypeptide or homolog(s) can be detected by any of a variety of art-known methods. For example, an antibody that specifically binds a B-ydcB or S-ydcB polypeptide can be used in an immunoassay. If desired, the antibody can be labeled (e.g., fluorescently or with a radioisotope) and detected directly (see, e.g., West and McMahon, *J. Cell Biol.* 74:264, 1977). Alternatively, a second antibody can be used for detection (e.g., a labeled antibody that binds the Fc portion of an anti-S-ydcB antibody). In an alternative detection method, the S-ydcB or B-ydcB polypeptide is labeled, and the label is detected (e.g., by labeling the S-ydcB or B-ydcB polypeptide with a radioisotope, fluorophore, chromophore, or the like). In still another method, the B-ydcB or S-ydcB polypeptide is produced as a fusion protein with a protein that can be detected optically, e.g., green fluorescent protein (which can be detected under UV light). In an alternative method, the S-ydcB or B-ydcB can be produced as a fusion protein with an enzyme having a detectable enzymatic activity, such as horse radish peroxidase, alkaline phosphatase, β-galactosidase, or glucose oxidase. Genes encoding all of these enzymes have been cloned and are readily available for use by those of skill in the art. If desired, the fusion protein can include an antigen, and such an antigen can be detected and measured with a polyclonal or monoclonal antibody using conventional methods. Suitable antigens include enzymes (e.g., horse radish peroxidase, alkaline phosphatase, and β-galactosidase) and non-enzymatic polypeptides (e.g., serum proteins, such as BSA and globulins, and milk proteins, such as caseins).

In various in vivo methods for identifying polypeptides that bind S-ydcB of B-ydcB or homologs thereof, the conventional two-hybrid assays of protein/protein interactions can be used (see e.g., Chien et al., *Proc. Natl. Acad. Sci. USA*, 88:9578, 1991; Fields et al., U.S. Pat. No. 5,283, 173; Fields and Song, Nature, 340:245, 1989; Le Douarin et al., *Nucleic Acids Research*, 23:876, 1995; Vidal et al., *Proc. Natl. Acad. Sci. USA*, 93:10315–10320, 1996; and White, *Proc. Natl. Acad. Sci. USA*, 93:10001–10003, 1996). Generally, the two-hybrid methods involve in vivo reconstitution of two separable domains of a transcription factor. One fusion protein contains the S-ydcB or B-ydcB polypeptide (or homolog thereof) fused to either a transactivator domain or DNA binding domain of a transcription factor (e.g., of Gal4). The other fusion protein contains a test polypeptide fused to either the DNA binding domain or a transactivator domain of a transcription factor. Once brought together in a single cell (e.g., a yeast cell or mammalian cell), one of the fusion proteins contains the transactivator domain and the other fusion protein contains the DNA binding domain. Therefore, binding of the S-ydcB or B-ydcB polypeptide or homolog to the test polypeptide (i.e., candidate antibacterial agent) reconstitutes the transcription factor. Reconstitution of the transcription factor can be detected by detecting expression of a gene (i.e., a reporter gene) that is operably linked to a DNA sequence that is bound by the DNA binding domain of the transcription factor. Kits for practicing various two-hybrid methods are commercially available (e.g., from Clontech; Palo Alto, Calif.).

The methods described above can be used for high throughput screening of numerous test compounds to identify candidate antibacterial (or anti-bacterial) agents. Having. identified a test compound as a candidate antibacterial agent, the candidate antibacterial agent can be further tested for inhibition of bacterial growth in vitro or in vivo (e.g., using an animal, e.g., rodent, model system) if desired. Using other, art-known variations of such methods, one can test the ability of a nucleic acid (e.g., DNA or RNA) used as the test compound to bind S-ydcB or B-ydcB or a homolog thereof.

In vitro, further testing can be accomplished by means known to those in the art such as an enzyme inhibition assay or a whole-cell bacterial growth inhibition assay. For example, an agar dilution assay identifies a substance that inhibits bacterial growth. Microtiter plates are prepared with serial dilutions of the test compound, adding to the preparation a given amount of growth substrate, and providing a preparation of bacteria. Inhibition of bacterial growth is determined, for example, by observing changes in optical densities of the bacterial cultures.

Inhibition of bacterial growth is demonstrated, for example, by comparing (in the presence and absence of a test compound) the rate of growth or the absolute growth of bacterial cells. Inhibition includes a reduction of one of the above measurements by at least 20%. Particularly potent test compounds may further reduce the growth rate (e.g., by at least 25%, 30%, 40%, 50%, 75%, 80%, or 90%).

Rodent (e.g., murine) and rabbit animal models of bacterial infections are known to those of skill in the art, and such animal model systems are accepted for screening antibacterial agents as an indication of their therapeutic efficacy in human patients. In a typical in vivo assay, an animal is infected with a pathogenic strain of bacteria, e.g., by inhalation of bacteria such as *Streptococcus pneumoniae*, and conventional methods and criteria are used to diagnose the mammal as being afflicted with a bacterial infection. The candidate antibacterial agent then is administered to the mammal at a dosage of 1–100 mg/kg of body weight, and the mammal is monitored for signs of amelioration of disease. Alternatively, the test compound can be administered to the mammal prior to infecting the mammal with the bacteria, and the ability of the treated mammal to resist infection is measured. Of course, the results obtained in the presence of the test compound should be compared with results in control animals, which are not treated with the test compound. Administration of candidate antibacterial agents to the mammal can be carried out as described below, for example.

Pharmaceutical Formulations

Treatment includes administering a pharmaceutically effective amount of a composition containing an antibacterial agent to a subject in need of such treatment, thereby inhibiting bacterial growth in the subject. Such a composition typically contains from about 0.1 to 90% by weight (such as 1 to 20% or 1 to 10%) of an antibacterial agent of the invention in a pharmaceutically acceptable carrier.

Solid formulations of the compositions for oral administration may contain suitable carriers or excipients, such as corn starch, gelatin, lactose, acacia, sucrose, microcrystalline cellulose, kaolin, mannitol, dicalcium phosphate, calcium carbonate, sodium chloride, or alginic acid. Disintegrators that can be used include, without limitation, microcrystalline cellulose, corn starch, sodium starch glycolate and alginic acid. Tablet binders that may be used include acacia, methylcellulose, sodium carboxymethylcellulose, polyvinylpyrrolidone (Povidone), hydroxypropyl methylcellulose, sucrose, starch, and ethylcellulose. Lubricants that may be used include magnesium stearates, stearic acid, silicone fluid, talc, waxes, oils, and colloidal silica.

Liquid formulations of the compositions for oral administration prepared in water or other aqueous vehicles may contain various suspending agents such as methylcellulose, alginates, tragacanth, pectin, kelgin, carrageenan, acacia, polyvinylpyrrolidone, and polyvinyl alcohol. The liquid formulations may also include solutions, emulsions, syrups and elixirs containing, together with the active compound(s), wetting agents, sweeteners, and coloring and flavoring agents. Various liquid and powder formulations can be prepared by conventional methods for inhalation into the lungs of the mammal to be treated.

Injectable formulations of the compositions may contain various carriers such as vegetable oils, dimethylacetamide, dimethylformamide, ethyl lactate, ethyl carbonate, isopropyl myristate, ethanol, polyols (glycerol, propylene glycol, liquid polyethylene glycol, and the like). For intravenous injections, water soluble versions of the compounds may be administered by the drip method, whereby a pharmaceutical formulation containing the antibacterial agent and a physiologically acceptable excipient is infused. Physiologically acceptable excipients may include, for example, 5% dextrose, 0.9% saline, Ringer's solution or other suitable excipients. Intramuscular preparations, a sterile formulation of a suitable soluble salt form of the compounds can be dissolved and administered in a pharmaceutical excipient such as Water-for-Injection, 0.9% saline, or 5% glucose solution. A suitable insoluble form of the compound may be prepared and administered as a suspension in an aqueous base or a pharmaceutically acceptable oil base, such as an ester of a long chain fatty acid, (e.g., ethyl oleate).

A topical semi-solid ointment formulation typically contains a concentration of the active ingredient from about 1 to 20%, e.g., 5 to 10% in a carrier such as a pharmaceutical cream base. Various formulations for topical use include drops, tinctures, lotions, creams, solutions, and ointments containing the active ingredient and various supports and vehicles.

The optimal percentage of the antibacterial agent in each pharmaceutical formulation varies according to the formulation itself and the therapeutic effect desired in the specific pathologies and correlated therapeutic regimens. Appropriate dosages of the antibacterial agents can be readily determined by those of ordinary skill in the art of medicine by monitoring the mammal for signs of disease amelioration or inhibition, and increasing or decreasing the dosage and/or frequency of treatment as desired. The optimal amount of the antibacterial compound used for treatment of conditions caused by or contributed to by bacterial infection may depend upon the manner of administration, the age and the body weight of the subject, and the condition of the subject to be treated. Generally, the antibacterial compound is administered at a dosage of 1 to 100 mg/kg of body weight, and typically at a dosage of 1 to 10 mg/kg of body weight.

Identification of Homologs of S-ydcB and B-ydcB in Additional Bacterial Strains

Now that the S-ydcB and B-ydcB genes have been identified as essential for survival, these genes, or fragments thereof, can be used to detect homologous or genes in other strains. In particular, these genes can be used to analyze various pathogenic and non-pathogenic strains of bacteria, particularly gram-positive bacteria. Fragments of a nucleic acid (DNA or RNA) encoding an S-ydcB or B-ydcB polypeptide or homolog (or sequences complementary thereto) can be used as probes in conventional nucleic acid hybridization assays of nucleic acids from bacteria. For example, nucleic acid probes (which typically are 8–30, or usually 15–20, nucleotides in length) can be used to detect homologs in art-known molecular biology methods, such as Southern blotting, Northern blotting, dot or slot blotting, PCR amplification methods, colony hybridization methods, and the like. Typically, an oligonucleotide probe based on the nucleic acid sequences described herein, or fragments thereof, is labeled and used to screen a genomic library constructed from mRNA obtained from a bacterial strain of interest. A suitable method of labeling involves using polynucleotide kinase to add $^{32}$P-labeled ATP to the oligonucleotide used as the probe. This method is well known in the art, as are several other suitable methods (e.g., biotinylation and enzyme labeling).

Hybridization of the oligonucleotide probe to the library, or other nucleic acid sample, typically is performed under moderate to highly stringent conditions. Nucleic acid duplex or hybrid stability is expressed as the melting temperature or $T_m$, which is the temperature at which a probe dissociates from a target DNA. This melting temperature is used to define the required stringency conditions. If sequences are to be identified that are related and substantially identical to the probe, rather than identical, then it is useful to first establish the lowest temperature at which only homologous hybridization occurs with a particular concentration of salt (e.g., SSC or SSPE). Then, assuming that 1% mismatching results in a 1° C. decrease in the $T_m$, the temperature of the final wash in the hybridization reaction is reduced accordingly (for example, if sequences having ≧95% identity with the probe are sought, the final wash temperature is decreased by 5° C.). In practice, the change in $T_m$ can be between 0.50 and 1.5° C. per 1% mismatch.

High stringency hybridization conditions include, for example, hybridizing at. 68° C. in 5×SSC/5×Denhardt's solution/1.0% SDS, or in 0.5 M NaHPO$_4$ (pH 7.2)/1 mM EDTA/7% SDS, or in 50% formamide/0.25 M NaHPO$_4$ (pH 7.2)/0.25 M NaCl/1 mM EDTA/7% SDS; and washing in 0.2×SSC/0.1% SDS at room temperature or at 42° C., or in 0.1×SSC/0.1% SDS at 68° C., or in 40 mM NaHPO$_4$ (pH 7.2)/1 mM EDTA/5% SDS at 50° C., or in 40 mM NaHPO$_4$ (pH 7.2) 1 mM EDTA/1% SDS at 50° C. Moderately stringent conditions include washing in 3×SSC at 42° C. The parameters of salt concentration and temperature can be varied to achieve the optimal level of identity between the probe and the target nucleic acid. Additional guidance regarding such conditions is readily available in the art, for example, by Sambrook et al., 1989, Molecular Cloning, A Laboratory Manual, Cold Spring Harbor Press, N.Y.; and Ausubel et al. (eds.), 1995, Current Protocols in Molecular Biology, (John Wiley & Sons, N.Y.) at Unit 2.10.

In one approach, libraries constructed from pathogenic or non-pathogenic bacterial strains can be screened. For example, such strains can be screened for expression of B-ydcB or S-ydcB genes by Northern blot analysis. Upon detection of transcripts of homologs of the S-ydcB or B-ydcB genes, libraries can be constructed from RNA isolated from the appropriate strain, utilizing standard techniques well known to those of skill in the art. Alternatively, a total genomic DNA library can be screened using an S-ydcB or B-ydcB gene probe (or a probe directed to a homolog thereof).

New gene sequences can be isolated, for example, by performing PCR using two degenerate oligonucleotide primer pools designed on the basis of nucleotide sequences within the S-ydcB gene, or its homologs, as described herein. The template for the reaction can be DNA obtained from strains suspected of expressing a homolog of S-ydcB or B-ydcB. The PCR product can be subcloned and sequenced to ensure that the amplified sequences represent the sequences of a new homolog.

Synthesis of an S-ydcB or B-ydcB polypeptide or homolog thereof (or a fragment thereof (e.g., an antigenic fragment)) can readily be accomplished using any of the various art-known techniques. For example, an S-ydcB or B-ydcB polypeptide or homolog thereof, or a fragment(s), can be synthesized chemically in vitro, or enzymatically (e.g., by in vitro transcription and translation). Alternatively, the gene can be expressed in, and the polypeptide purified from, a cell (e.g., a cultured cell) by using any of the numerous, available gene expression systems. For example, the polypeptide can be produced in a prokaryotic host (e.g., *E. coli* or *B. subtilis*) or in eukaryotic cells, such as yeast cells or in insect cells (e.g., by using a baculovirus-based expression vector).

Proteins and polypeptides can also be produced in plant cells, if desired. For plant cells, viral expression vectors (e.g., cauliflower mosaic virus and tobacco mosaic virus) and plasmid expression vectors (e.g., Ti plasmid) are suitable. Such cells are available from a wide range of sources (e.g., the American Type Culture Collection, Rockland, Md.; also, see, e.g., Ausubel et al., Current Protocols in Molecular Biology, John Wiley & Sons, New York, 1994). The optimal methods of transformation or transfection and the choice of expression vehicle will depend on the host system selected. Transformation and transfection methods are described, e.g., in Ausubel et al., supra; expression vehicles may be chosen from those provided, e.g., in Cloning Vectors: A Laboratory Manual (P. H. Pouwels et al., 1985, Supp. 1987). The host cells harboring the expression vehicle can be cultured in conventional nutrient media, adapted as needed for activation of a chosen gene, repression of a chosen gene, selection of transformants, or amplification of a chosen gene.

If desired, an S-ydcB or B-ydcB polypeptide or homolog can be produced as a fusion protein. For example, the expression vector pUR278 (Ruther et al., EMBO J., 2:1791, 1983) can be used to create lacZ fusion proteins. The art-known pGEX vectors can be used to express foreign polypeptides as fusion proteins with glutathione S-transferase (GST). In general, such fusion proteins are soluble and can be easily purified from lysed cells by adsorption to glutathione-agarose beads followed by elution in the presence of free glutathione. The pGEX vectors are designed to include thrombin or factor Xa protease cleavage sites so that the cloned target gene product can be released from the GST moiety.

In an exemplary expression system, a baculovirus such as *Autographa californica* nuclear polyhedrosis virus (AcNPV), which grows in *Spodoptera frugiperda* cells, can be used as a vector to express foreign genes. A coding sequence encoding an S-ydcB .or B-ydcB polypeptide or homolog can be cloned into a non-essential region (for example the polyhedrin gene) of the viral genome and placed under control of a promoter, e.g., the polyhedrin promoter or an exogenous promoter. Successful insertion of a gene encoding an S-ydcB or B-ydcB polypeptide or homolog can result in inactivation of the polyhedrin gene and production of non-occluded recombinant virus (i.e., virus lacking the proteinaceous coat encoded by the polyhedrin gene). These recombinant viruses are then typically used to infect insect cells (e.g., Spodoptera frugiperda cells) in which the inserted gene is expressed (see, e.g., Smith et al., *J. Virol.*, 46:584, 1983; Smith, U.S. Pat. No. 4,215,051). If desired, mammalian cells can be used in lieu of insect cells, provided that the virus is engineered such that the gene encoding the desired polypeptide is placed under the control of a promoter that is active in mammalian cells.

In mammalian host cells, a number of viral-based expression systems can be utilized. When an adenovirus is used as an expression vector, the nucleic acid sequence encoding the B-ydcB or S-ydcB polypeptide or homolog can be ligated to an adenovirus transcription/translation control complex, e.g., the late promoter and tripartite leader sequence. This chimeric gene can then be inserted into the adenovirus genome by in vitro or in vivo recombination. Insertion into a non-essential region of the viral genome (e.g., region E1 or E3) will result in a recombinant virus that is viable and capable of expressing B-ydcB or S-ydcB gene products in infected hosts (see, e.g., Logan, Proc. Natl. Acad. Sci. USA, 81:3655, 1984).

Specific initiation signals may be required for efficient translation of inserted nucleic acid sequences. These signals include the ATG initiation codon and adjacent sequences. In general, exogenous translational control signals, including, perhaps, the ATG initiation codon, should be provided. Furthermore, the initiation codon must be in phase with the reading frame of the desired coding sequence to ensure translation of the entire sequence. These exogenous translational control signals and initiation codons can be of a variety of origins, both natural and synthetic. The efficiency of expression may be enhanced by the inclusion of appropriate transcription enhancer elements, or transcription terminators (Bittner et al., *Methods in Enzymol.*, 153:516, 1987).

The S-ydcB and B-ydcB polypeptides and homologs can be expressed individually or as fusions with a heterologous polypeptide, such as a signal sequence or other polypeptide having a specific cleavage site at the N-and/or C-terminus of the protein or polypeptide. The heterologous signal sequence selected should be one that is recognized and processed, i.e., cleaved by a signal peptidase, by the host cell in which the fusion protein is expressed.

A host cell can be chosen that modulates the expression of the inserted sequences, or modifies and processes the gene product in a specific, desired fashion. Such modifications and processing (e.g., cleavage) of protein products may facilitate optimal functioning of the protein. Various host cells have characteristic and specific mechanisms for post-translational processing and modification of proteins and gene products. Appropriate cell lines or host systems familiar to those of skill in the art of molecular biology can be chosen to ensure the correct modification and processing of the foreign protein expressed. To this end, eukaryotic host cells that possess the cellular machinery for proper processing of the primary transcript, and phosphorylation of the gene product can be used. Such mammalian host cells include, but are not limited to, CHO, VERO, BHK, HeLa, COS, MDCK, 293, 3T3, WI38, and choroid plexus cell lines.

If desired, the S-ydcB or B-ydcB polypeptide or homolog can be produced by a stably-transfected mammalian cell line. A number of vectors suitable for stable transection of mammalian cells are available to the public, see, e.g., Pouwels et al. (supra); methods for constructing such cell lines are also publicly known, e.g., in Ausubel et al. (supra). In one example, DNA encoding the protein is cloned into an expression vector that includes the dihydrofolate reductase (DHFR) gene. Integration of the plasmid and, therefore, the B-ydcB or S-ydcB polypeptide-encoding gene into the host cell chromosome is selected for by including 0.01–300 $\mu$M methotrexate in the cell culture medium (as described in Ausubel et al., supra). This dominant selection can be accomplished in most cell types.

Recombinant protein expression can be increased by DHFR-mediated amplification of the transfected gene. Methods for selecting cell lines bearing gene amplifications are described in Ausubel et al. (supra); such methods generally involve extended culture in medium containing gradually increasing levels of methotrexate. DHFR-containing expression vectors commonly used for this purpose include pCVSEII-DHFR and pAdD26SV(A) (described in Ausubel et al., supra).

A number of other selection systems can be used, including but not limited to, herpes simplex virus thymidine kinase genes, hypoxanthine-guanine phosphoribosyltransferase genes, and adenine phosphoribosyltransferase genes, which can be employed in tk, hgprt, or aprt cells, respectively. In addition, gpt, which confers resistance to mycophenolic acid (Mulligan et al., *Proc. Natl. Acad. Sci. USA*, 78:2072, 1981); neo, which confers resistance to the aminoglycoside G-418 (Colberre-Garapin et al., *J. Mol. Biol.*, 150:1, 1981); and hygro, which confers resistance to hygromycin (Santerre et al., *Gene*, 30:147, 1981), can be used.

Given the amino acid sequences described herein, polypeptides useful in practicing the invention, particularly fragments of B-ydcB or S-ydcB polypeptides, can be produced by standard chemical synthesis (e.g., by the methods described in *Solid Phase Peptide Synthesis*, 2nd ed., The Pierce Chemical Co., Rockford, Ill., 1984) and used as antigens, for example.

Other Embodiments

The invention also features fragments, variants, analogs, and derivatives of the S-ydcB and B-ydcB polypeptides described above that retain one or more of the biological activities of the S-ydcB and B-ydcB polypeptides, as determined, for example, in an assay of acyl carrier protein synthase activity. Included within the invention are naturally-occurring and non-naturally-occurring variants. Compared with the naturally-occurring gene sequences depicted in FIGS. 1 and 2, the nucleic acid sequences encoding variants may have a substitution, deletion, or addition of one or more nucleotides. The preferred variants retain a function of the S-ydcB or B-ydcB polypeptides, e.g., as determined in a complementation assay.

It is to be understood that, while the invention has been described in conjunction with the detailed description thereof, the foregoing description is intended to illustrate and not limit the scope of the invention, which is defined by the scope of the appended claims. Other aspects, advantages, and modifications are within the scope of the following claims. For example, other art-known assays to detect interactions of test compounds with proteins, or to detect inhibition of bacterial growth also can be used with the S-ydcB and B-ydcB genes, gene products and homologs thereof. Also included within the invention is a method of making a pharmaceutical composition for use in inhibiting bacterial activity. Specifically, such a method includes formulating a pharmaceutically acceptable excipient with an antibacterial agent, such as those described herein.

What is claimed is:

1. An isolated nucleic acid molecule encoding an S-ydcB polypeptide comprising the amino acid sequence of SEQ ID NO:2.

2. A host cell comprising an exogenously introduced nucleic acid molecule of claim 1.

3. An isolated nucleic acid molecule of claim 1, wherein the nucleic acid molecule comprises the nucleotide sequence of SEQ ID NO:1, or degenerate variants thereof that encode the amino acid sequence of SEQ ID NO:2.

4. A vector comprising a nucleic acid molecule of claim 1.

5. An expression vector comprising a nucleic acid molecule of claim 1 operably linked to a nucleotide sequence regulatory element that controls expression of said nucleic acid molecule.

6. A host cell of claim 2, wherein the cell is a yeast or bacterium.

7. A genetically engineered host cell comprising a nucleic acid molecule of claim 1 operably linked to a heterologous nucleotide sequence regulatory element that controls expression of the nucleic acid molecule in the host cell.

8. A host cell of claim 7, wherein the cell is a yeast or bacterium.

9. An isolated nucleic acid molecule encoding the amino acid sequence of SEQ ID NO:2, as depicted in FIG. 1.

10. An isolated nucleic acid molecule of claim 9, wherein the nucleic acid molecule consists of the nucleotide sequence of SEQ ID NO:1, as depicted in FIG. 1.

11. A host cell comprising an exogenously introduced nucleic acid molecule of claim 9.

12. A vector comprising a nucleic acid molecule of claim 9.

13. An expression vector comprising a nucleic acid molecule of claim 9, operably linked to a nucleotide sequence regulatory element that controls expression of said nucleic acid molecule.

14. An isolated nucleic acid molecule of at least 471 nucleotides in length that hybridizes under high stringency hybridization conditions to SEQ ID NO:1, wherein a nucleic acid sequence complementary to the nucleic acid molecule encodes a polypeptide having acyl carrier protein synthase activity, and wherein high stringency hybridization conditions include hybridizing at 68° C. in 5×SSC/5×Denhardt's solution/1.0% SDS, or in 0.5 M NaHPO$_4$ (pH 7.2)/1 mM EDTA/7% SDS, or in 50% formamide/0.25 M NaHPO$_4$ (pH 7.2)/0.25 M NaCl/1 mM EDTA/7% SDS; and washing in 0.2×SSC/0.1% SDS at room temperature or at 42° C., or in 0.1×SSC/0.1% SDS at 68° C., or in 40 mM NaHPO$_4$ (pH 7.2)/1 mM EDTA/5% SDS at 50° C., or in 40 mM NaHPO$_4$ (pH 7.2) 1 mM EDTA/1% SDS at 50° C.

15. An isolated nucleic acid molecule that is fully complementary to a nucleic acid molecule that encodes the amino acid sequence of SEQ ID NO:2.

16. An isolated nucleic acid molecule of claim 15, wherein the nucleic acid molecule is fully complementary to SEQ ID NO:1.

17. A host cell comprising an exogenously introduced nucleic acid molecule of claim 14.

18. A vector comprising a nucleic acid molecule of claim 14.

19. An expression vector comprising a nucleic acid molecule of claim 14, operably linked to a nucleotide sequence regulatory element that controls expression of said nucleic acid molecule.

* * * * *

SEQUENCE LISTING

<160> NUMBER OF SEQ ID NOS: 12

<210> SEQ ID NO 1
<211> LENGTH: 471
<212> TYPE: DNA
<213> ORGANISM: Streptococcus pneumonia
<220> FEATURE:
<221> NAME/KEY: CDS
<222> LOCATION: (1)...(468)

<400> SEQUENCE: 1

| ttg cct agg ttg gga aaa tac aga ggc ctt ggt aga aga gat tta tgt | 48 |
| Leu Pro Arg Leu Gly Lys Tyr Arg Gly Leu Gly Arg Arg Asp Leu Cys | |
| 1               5                   10                  15     | |

| tac ctt gac aaa ata agt gaa aag gat gga gtt ggg gaa tct caa ctc | 96 |
| Tyr Leu Asp Lys Ile Ser Glu Lys Asp Gly Val Gly Glu Ser Gln Leu | |
|                 20                  25                  30     | |

| ctt ttg atg aga atg ata gtt gga cac gga att gac atc gaa gaa ttg | 144 |
| Leu Leu Met Arg Met Ile Val Gly His Gly Ile Asp Ile Glu Glu Leu | |
|         35                  40                  45             | |

| gct tcg ata gaa agc gca gtt aca cga cat gaa gga ttt gct aag cgt | 192 |
| Ala Ser Ile Glu Ser Ala Val Thr Arg His Glu Gly Phe Ala Lys Arg | |
|     50                  55                  60                 | |

| gta ctg acc gct cag gaa atg gag cgc ttc acc agt ctc aaa gga cgc | 240 |
| Val Leu Thr Ala Gln Glu Met Glu Arg Phe Thr Ser Leu Lys Gly Arg | |
| 65                  70                  75                  80 | |

| agg caa ata gaa tat tta gct ggt cgc tgg tcg gct aag gag gcc ttt | 288 |
| Arg Gln Ile Glu Tyr Leu Ala Gly Arg Trp Ser Ala Lys Glu Ala Phe | |
|                 85                  90                  95     | |

| tcc aag gct atg gga acg ggc att agc aag ctc ggt ttt cag gat ttg | 336 |
| Ser Lys Ala Met Gly Thr Gly Ile Ser Lys Leu Gly Phe Gln Asp Leu | |
|         100                 105                 110            | |

| gaa gtc ttg aac aat gaa cgt ggg gcg cct tat ttt agt cag gca cca | 384 |
| Glu Val Leu Asn Asn Glu Arg Gly Ala Pro Tyr Phe Ser Gln Ala Pro | |
|     115                 120                 125                | |

| ttt tca gga aag att tgg ctg tct atc agc cac acc gat cag ttt gtg | 432 |
| Phe Ser Gly Lys Ile Trp Leu Ser Ile Ser His Thr Asp Gln Phe Val | |
| 130                 135                 140                    | |

| aca gcc agt gtc att ttg gag gaa aat cat gaa agc tag             | 471 |
| Thr Ala Ser Val Ile Leu Glu Glu Asn His Glu Ser                 | |
| 145                 150                 155                    | |

<210> SEQ ID NO 2
<211> LENGTH: 156
<212> TYPE: PRT
<213> ORGANISM: Streptococcus pneumonia

<400> SEQUENCE: 2

Leu Pro Arg Leu Gly Lys Tyr Arg Gly Leu Gly Arg Arg Asp Leu Cys
1               5                   10                  15

Tyr Leu Asp Lys Ile Ser Glu Lys Asp Gly Val Gly Glu Ser Gln Leu
                20                  25                  30

Leu Leu Met Arg Met Ile Val Gly His Gly Ile Asp Ile Glu Glu Leu
        35                  40                  45

Ala Ser Ile Glu Ser Ala Val Thr Arg His Glu Gly Phe Ala Lys Arg
    50                  55                  60

Val Leu Thr Ala Gln Glu Met Glu Arg Phe Thr Ser Leu Lys Gly Arg
65                  70                  75                  80

Arg Gln Ile Glu Tyr Leu Ala Gly Arg Trp Ser Ala Lys Glu Ala Phe

```
                        85                  90                  95
Ser Lys Ala Met Gly Thr Gly Ile Ser Lys Leu Gly Phe Gln Asp Leu
            100                 105                 110

Glu Val Leu Asn Asn Glu Arg Gly Ala Pro Tyr Phe Ser Gln Ala Pro
            115                 120                 125

Phe Ser Gly Lys Ile Trp Leu Ser Ile Ser His Thr Asp Gln Phe Val
            130                 135                 140

Thr Ala Ser Val Ile Leu Glu Glu Asn His Glu Ser
145                 150                 155

<210> SEQ ID NO 3
<211> LENGTH: 366
<212> TYPE: DNA
<213> ORGANISM: Streptococcus pneumonia
<220> FEATURE:
<221> NAME/KEY: CDS
<222> LOCATION: (1)...(363)

<400> SEQUENCE: 3 atg att tac ggc att ggg ctg gac att acc gag ctt aaa cgg atc gcc    48
Met Ile Tyr Gly Ile Gly Leu Asp Ile Thr Glu Leu Lys Arg Ile Ala
 1               5                  10                  15 tct atg gct ggg cgc cag aaa agg ttt gcc gag cgg att ttg acg cga    96
Ser Met Ala Gly Arg Gln Lys Arg Phe Ala Glu Arg Ile Leu Thr Arg
            20                  25                  30 agc gag ctt gac caa tac tat gag ctt tca gag aaa aga aaa aac gaa   144
Ser Glu Leu Asp Gln Tyr Tyr Glu Leu Ser Glu Lys Arg Lys Asn Glu
        35                  40                  45 ttt ctc gcg ggc aga ttc gcg gca aaa gaa gcg ttc tcg aaa gca ttt   192
Phe Leu Ala Gly Arg Phe Ala Ala Lys Glu Ala Phe Ser Lys Ala Phe
    50                  55                  60 ggc acc ggc att ggg agg cag ctc agc ttt cag gac att gaa att agg   240
Gly Thr Gly Ile Gly Arg Gln Leu Ser Phe Gln Asp Ile Glu Ile Arg
65                  70                  75                  80 aaa gac caa aat ggc aag ccc tat atc att tgt acg aaa ctg agc cag   288
Lys Asp Gln Asn Gly Lys Pro Tyr Ile Ile Cys Thr Lys Leu Ser Gln
                85                  90                  95 gcc gcc gtt cac gta tcg atc act cat aca aaa gaa tac gct gcc gcg   336
Ala Ala Val His Val Ser Ile Thr His Thr Lys Glu Tyr Ala Ala Ala
            100                 105                 110 cag gtt gtg att gaa agg ttg tca agc tag                           366
Gln Val Val Ile Glu Arg Leu Ser Ser
        115                 120

<210> SEQ ID NO 4
<211> LENGTH: 121
<212> TYPE: PRT
<213> ORGANISM: Streptococcus pneumonia

<400> SEQUENCE: 4

Met Ile Tyr Gly Ile Gly Leu Asp Ile Thr Glu Leu Lys Arg Ile Ala
 1               5                  10                  15

Ser Met Ala Gly Arg Gln Lys Arg Phe Ala Glu Arg Ile Leu Thr Arg
            20                  25                  30

Ser Glu Leu Asp Gln Tyr Tyr Glu Leu Ser Glu Lys Arg Lys Asn Glu
        35                  40                  45

Phe Leu Ala Gly Arg Phe Ala Ala Lys Glu Ala Phe Ser Lys Ala Phe
    50                  55                  60

Gly Thr Gly Ile Gly Arg Gln Leu Ser Phe Gln Asp Ile Glu Ile Arg
65                  70                  75                  80
```

```
Lys Asp Gln Asn Gly Lys Pro Tyr Ile Ile Cys Thr Lys Leu Ser Gln
                85                  90                  95

Ala Ala Val His Val Ser Ile Thr His Thr Lys Glu Tyr Ala Ala Ala
            100                 105                 110

Gln Val Val Ile Glu Arg Leu Ser Ser
        115                 120

<210> SEQ ID NO 5
<211> LENGTH: 21
<212> TYPE: DNA
<213> ORGANISM: Streptococcus pneumonia

<400> SEQUENCE: 5
gtgttcgtgc tgacttgcac c                                         21

<210> SEQ ID NO 6
<211> LENGTH: 21
<212> TYPE: DNA
<213> ORGANISM: Streptococcus pneumonia

<400> SEQUENCE: 6
gaattatttc ctcccgttaa a                                         21

<210> SEQ ID NO 7
<211> LENGTH: 20
<212> TYPE: DNA
<213> ORGANISM: Streptococcus pneumonia

<400> SEQUENCE: 7
ttaacgccat ctatgctgct                                           20

<210> SEQ ID NO 8
<211> LENGTH: 21
<212> TYPE: DNA
<213> ORGANISM: Streptococcus pneumonia

<400> SEQUENCE: 8
ttccgtgtcc aactatcatc c                                         21

<210> SEQ ID NO 9
<211> LENGTH: 21
<212> TYPE: DNA
<213> ORGANISM: Streptococcus pneumonia

<400> SEQUENCE: 9
agtttgtgac agccagtgtc a                                         21

<210> SEQ ID NO 10
<211> LENGTH: 21
<212> TYPE: DNA
<213> ORGANISM: Streptococcus pneumonia

<400> SEQUENCE: 10
tgattcctca tcagcagtag c                                         21

<210> SEQ ID NO 11
<211> LENGTH: 471
<212> TYPE: DNA
<213> ORGANISM: Streptococcus pneumonia

<400> SEQUENCE: 11
aacggatcca acccttttat gtctccggaa ccatcttctc taaatacaat ggaactgttt    60
```

-continued

```
tattcactttt tcctacctca acccttaga gttgaggaaa actactctta ctatcaacct     120
gtgccttaac tgtagcttct taaccgaagc tatctttcgc gtcaatgtgc tgtacttcct     180
aaacgattcg cacatgactg gcgagtcctt tacctcgcga agtggtcaga gtttcctgcg     240
tccgtttatc ttataaatcg accagcgacc agccgattcc tccggaaaag gttccgatac     300
ccttgcccgt aatcgttcga gccaaaagtc ctaaaccttc agaacttgtt acttgcaccc     360
cgcggaataa aatcagtccg tggtaaaagt cctttctaaa ccgacagata gtcggtgtgg     420
ctagtcaaac actgtcggtc acagtaaaac ctccttttag tactttcgat c             471
```

<210> SEQ ID NO 12
<211> LENGTH: 366
<212> TYPE: DNA
<213> ORGANISM: Streptococcus pneumonia

<400> SEQUENCE: 12

```
tactaaatgc cgtaacccga cctgtaatgg ctcgaatttg cctagcggag ataccgaccc      60
gcggtctttt ccaaacggct cgcctaaaac tgcgcttcgc tcgaactggt tatgatactc     120
gaaagtctct tttcttttt gcttaaagag cgcccgtcta agcgccgttt tcttcgcaag     180
agctttcgta aaccgtggcc gtaaccctcc gtcgagtcga aagtcctgta actttaatcc     240
tttctggttt taccgttcgg gatatagtaa acatgctttg actcggtccg gcggcaagtg     300
catagctagt gagtatgttt tcttatgcga cggcgcgtcc aacactaact ttccaacagt     360
tcgatc                                                               366
```